United States Patent [19]

Drucker

[11] Patent Number: 5,324,301
[45] Date of Patent: Jun. 28, 1994

[54] SURGICAL CUTTING INSTRUMENT WITH TIN-NICKLE ALLOY COATING AS AN ELONGATE BEARING SURFACE

[75] Inventor: Karen Drucker, Danville, N.H.

[73] Assignee: Smith & Nephew Dyonics, Inc., Andover, Mass.

[21] Appl. No.: 951,808

[22] Filed: Sep. 28, 1992

[51] Int. Cl.⁵ ............................................. A61B 17/32
[52] U.S. Cl. .................... 606/180; 606/170; 604/22
[58] Field of Search ................... 384/13, 25, 261, 280, 384/445, 625, 907; 428/646, 686, 926, 935; 606/168, 170, 171, 180; 604/22

[56] References Cited

U.S. PATENT DOCUMENTS 3,950,141 4/1976 Roemer ............................. 428/643
4,745,035 5/1988 Saurer et al. .
4,923,441 5/1990 Shuler ................................. 604/22

FOREIGN PATENT DOCUMENTS 2108154 5/1983 United Kingdom .

OTHER PUBLICATIONS

1985 Annual Book of ASTM Standards, Section 2, vol. 02.05, pp. 480–483.
Electroplating Engineering Handbook, Third Edition, Van Nostrand Reinhold Company, 1971, pp. 231–235, 251.
Kirk–Othmer Encyclopedia Of Chemical Technology, vol. 8, 1979 pp. 857–858.
"Blade Engineering for Flawless Performance", Smith & Nephew Dyonics Inc. 1992.

Primary Examiner—C. Fred Rosenbaum
Assistant Examiner—N. Kent Gring
Attorney, Agent, or Firm—Rosenman & Colin

[57] ABSTRACT

A surgical instrument comprising inner and outer tubular members has a coating of tin-nickel alloy on the outer surface of the inner tubular member and/or the inner surface of the outer tubular member to provide an elongate bearing surface between the tubular members.

5 Claims, 1 Drawing Sheet

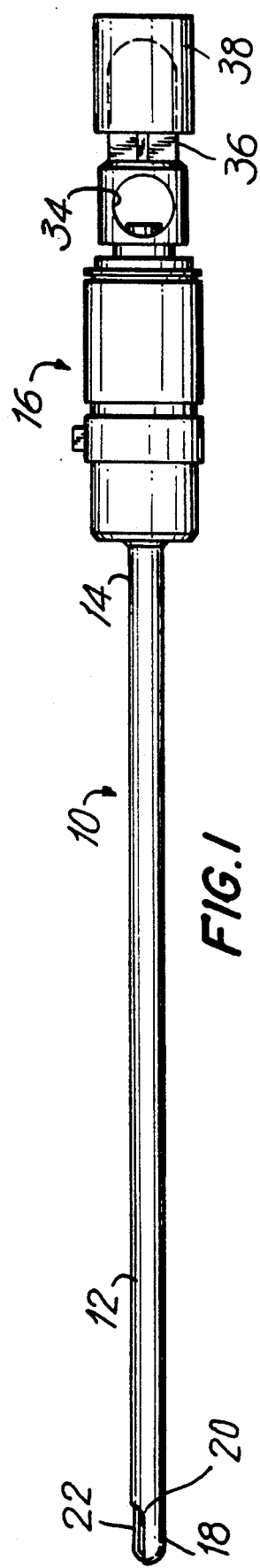
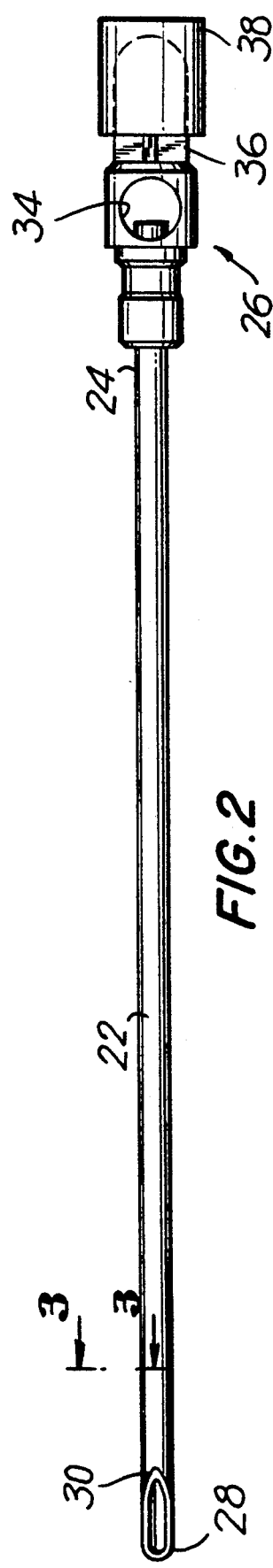

SURGICAL CUTTING INSTRUMENT WITH TIN-NICKLE ALLOY COATING AS AN ELONGATE BEARING SURFACE

The present invention relates to surgical cutting instruments and, more particularly, to surgical cutting instruments having elongate, inner and outer tubular members with distal ends cooperating to cut or resect bodily tissue, the cut tissue being aspirated through the inner member.

The use of elongate surgical cutting instruments has become well accepted in performing closed surgery, such as endoscopic surgery, e.g., arthroscopic surgery. Surgical cutting instruments for use in closed surgery conventionally have an elongate outer tubular member terminating at a distal end having an opening in the side wall and/or the end wall to form a cutting port or window and an elongate inner tubular member coaxially disposed in the outer tubular member and having a distal end disposed adjacent the opening in the distal end of the outer tubular member. The distal end of the inner tubular member has a surface or edge for engaging tissue via the opening in the distal end of the outer tubular member and in many cases cooperates with the opening to shear or cut tissue. The inner tubular member is rotatably driven at its proximal end, normally via a handpiece having a small electric motor therein controlled by finger-actuated switches on the handpiece, a foot switch or switches on a console supply power to the handpiece.

The distal end of the inner tubular member can have various configurations dependent upon the surgical procedure to be performed, and the opening in the distal end of the outer tubular member has a configuration to cooperate with the particular configurations of the distal end of the inner tubular member. For example, the inner and outer tubular members can be configured to produce whisker cutting, synovial resection, arthroplasty burring or abrading, side cutting, meniscus cutting, trimming, full radius resection, end cutting and the like, and the various configurations are referred to herein generically as "cutting blades or edges". Cut tissue is aspirated through the lumen of the inner tubular member to be collected via a tube communicating with the handpiece.

Surgical instruments of this type are commercially available wherein the outer diameter of the inner tubular member is substantially the same as the inner diameter of the outer tubular member, the inner and outer members being formed from electropolished stainless steel. Smith & Nephew Dyonics Inc. sells surgical cutting instruments having inner and outer electropolished stainless steel tubular members, wherein the outer surface of the electropolished stainless steel inner tubular member is coated with a thin layer of electroplated silver to maximize performance at high speeds.

It has now been found that a coating of electroplated tin-nickel alloy on the outer surface of the inner tubular member and/or the inner surface of the outer tubular member of the surgical cutting instrument markedly improves its performance at high speeds. The present invention thus provides a surgical cutting instrument having an elongate outer tubular member having outer and inner surfaces, a proximal end, a distal end and an opening disposed at the distal end; an elongate inner tubular member having outer and inner surfaces, a proximal end, a distal end and a cutting member disposed at the distal end, the inner tubular member being movably received in the outer tubular member to position the proximal end of the inner tubular member adjacent the proximal end of the outer tubular member, the distal end of the inner tubular member being adjacent the distal end of the outer tubular member and the cutting member being adjacent to the opening to permit the cutting member to engage body tissue through the opening; and a coating of tin-nickel alloy electrodeposited on at least a portion of the outer surface of the inner member and/or the inner surface of the outer member, the tin-nickel alloy coating being operable to provide an elongate bearing surface between the tubular members of the surgical cutting instrument.

The present invention has numerous advantages. Thus, the use of the tin-nickel alloy coating improves performance of the surgical cutting instrument at high speeds. Moreover, the tin-nickel alloy coating can be deposited by conventional electroplating techniques in an economical manner. Further, the tin-nickel alloy coating can be sterilized by conventional processing. Of course, the tin-nickel alloy coating is non-cytotoxic, thus permitting its use on surgical cutting instruments.

The present invention is illustrated in terms of its preferred embodiments in the accompanying drawing, in which:

FIG. 1 is a side elevation of a surgical cutting instrument according to the present invention.

FIG. 2 is a side elevation of an inner tubular member of the surgical cutting instrument of FIG. 1;

FIG. 3 is a detail view in section, in enlarged scale, taken along lines 3—3 of FIG. 2; and FIG. 4 is a detail view, similar to FIG. 3, of another embodiment of the present invention.

Referring to FIG. 1, a surgical cutting instrument 10 according to the present invention includes an elongate tubular outer member 12 made of electropolished stainless steel and having a proximal end 14 fixed to a plastic hub 16 and a distal end 18 having an opening 20 therein forming a cutting port or window. An elongate tubular inner member 22 (FIG. 2) made of electropolished stainless steel is rotatably received in outer tubular member 12 and, as shown in FIG. 2, has a proximal end 24 fixed to a plastic hub 26 having a configuration to be received in a recess (not shown) in hub 16 and a distal end 28 having a cutting edge 30 formed thereon and positioned adjacent opening 20 such that the cutting 30 edge can engage bodily tissue. The hub 26 has a transversely extending passage 34 therethrough, the inner tubular member 22 extending through an axial bore in hub 26 to communicate with passage 34. A driven tang 36 within portion 38 is adapted to be driven by a rotating slotted drive shaft of an electric motor in a handpiece, as is conventional.

The opening 20 in the distal end of the outer tubular member 12 extends through the side and end walls to produce an edge cooperating with the cutting edge 30 formed on the distal end 28 of the inner tubular member 22 to form a full radius cutter. The opening 20 can have any desired configuration to cooperate with the configuration of the cutting edge or edges on the distal end of the inner tubular member, as is known, so as to form trimmers, meniscus cutters, end cutters, side cutters, full radius cutters, synovial resectors, whiskers, open end cutters, arthroplasty burrs, slotted whiskers, tapered burrs, oval burrs, punch forceps and the like. The surgical cutting instrument of the present invention can have any desirable hub configuration to be utilized with any drive system or handpiece capable of rotating or reciprocating an elongate inner tubular member within an elongate outer tubular member to cut or otherwise engage body tissue at the distal end and aspirate cut tissue through the lumen of the inner tubular member.

In operation, the inner tubular member 12 is rotatably driven in the outer tubular member 12 such that the cutting edge 30 engages body tissue via the cutting port or window formed by opening 20, and the cut tissue is aspirated through the lumen of the inner tubular member 22 to exit the surgical cutting instrument via passage 34 which communicates with a suction passage at the handpiece.

In accordance with the present invention, as shown in FIG. 3, the inner tubular member 22 has a tin-nickel alloy coating 40 electroplated on its electropolished outer surface. The distal ends 18,28 of the members 12,22 are closely spaced together in order to provide optimum cutting action, and hence the coating 40 will extend from the distal end 28 for a length sufficient to provide an elongate bearing surface between these closely spaced portions of the members 12,22. Usually, coating 40 will be along substantially the full length of the outer surface of the inner tubular member from the distal end 28, including the cutting edge 30, to the proximal end 24. However, a coating 40 may be sufficient only along the closely spaced members adjacent the distal end 28, if the members 12, 22 have sufficient clearance along the remainder of the members as to be free-running. The tin-nickel alloy cutting 40 preferably has a thickness of from about 0.00005 to about 0.0001 inch such that the outer diameter of inner tubular member 22 is substantially same as the inner diameter of outer tubular member 12, with the coating 40 engaging the inner surface of the outer tubular member to form a bearing, preferably along the length of the surgical cutting instrument. If desired, the coating 40 may be applied to the inner surface of the outer tubular member 12 (FIG. 4) or to both the outer surface of the inner tubular member 22 and the inner surface of the outer tubular member 12. The tin-nickel alloy coating 40 is shown of exaggerated thickness in FIGS. 3 and 4 since the coating is so thin that it cannot be illustrated if the figures are to scale.

As explained in ASTM B605-75, Standard Specification for Electrodeposited Coatings of Tin-Nickel Alloy, an electrodeposited tin-nickel alloy coating is a single-phase, metastable compound corresponding approximately to the formula SnNi. ASTM B605-75 requires that the deposit of tin-nickel alloy contain 65+5% tin and the remainder nickel. Coatings of tin-nickel alloy suitable for use in the present invention will preferably meet this standard of about 60 to about 70% tin and about 40% to about 30% nickel, although tin-nickel alloy coatings having more or less tin may be used.

Electroplating techniques for obtaining acceptable tin-nickel alloy coatings for use in the invention are well known in the art and are practiced by commercial electroplaters. See, e.g., Electroplating Engineering Handbook, Third Edition, A. Kenneth Graham, Editor, Van Nostrand Reinhold Company, 1971, pages 231-235 and 251 for a discussion of plating compositions and operating conditions, as well as the references listed at page 257 thereof relating to tin-nickel alloy plating. See also U.K. Patent Application GB 2,108,154.

Any suitable procedure may be used to electroplate the tin-nickel coating on the surface of the tubular member, such as those described in the literature referred to above. Generally, the surface will be degreased, cleaned and deoxidized before electroplating, as is known. Suitably, the surface to be electroplated may be vapor degreased, cleaned with a heavy duty steel cleaner at 4-6 volts for 5-10 minutes and then rinsed. The cleaned surface may be deoxidized with an alkaline deoxidizer at 50 amp/square foot for 5-10 minutes, rinsed, and thereafter treated with an acid activator before the tin-nickel alloy is electroplated.

EXAMPLE

Specimens of electropolished inner tubular members of the 4.5 mm full radius cutters of Smith & Nephew Dyonics Inc. were provided with a bearing surface of a coating of tin-nickel (65+5% tin: 35+5% nickel) electrodeposited directly onto the outer surface of the electropolished 304 stainless steel inner tubular member. The outside diameter of the inner tubular member (before coating) was 0.135 inches, the thickness of the electrodeposited coating of tin-nickel was from about 0.00005 to about 0.0001 inches, while the inner diameter of the 304 stainless steel outer tubular member was 0.136 inches. The electrodeposited tin-nickel alloy coating was electroplated over the entire length of the electropolished outer surface of the inner tubular member. The surgical instruments thus obtained showed superior performance at high speeds compared to the same surgical instruments without the tin-nickel alloy coating.

Two sets of samples of the inner tubular members electroplated with the tin-nickel alloy coating were satisfactorily sterilized, one using ethylene oxide and the other using 5.00 to 6.00 M.rad. of gamma radiation.

What is claimed is:

1. A surgical cutting instrument comprising an elongate outer tubular member having outer and inner surfaces, a proximal end, a distal end and an opening disposed at said distal end; an elongate inner tubular member having outer and inner surfaces, a proximal end, a distal end and a cutting member at said distal end, the inner tubular member being movably received in said outer tubular member to position said proximal and distal ends of said inner tubular member adjacent said proximal and distal ends of said outer tubular member, respectively, said cutting member being adjacent said opening to permit said cutting member to engage bodily tissue through said opening; and a coating of tin-nickel alloy electroplated on at least a portion of said outer surface of said inner tubular member and/or said inner surface of said outer tubular member, said tin-nickel alloy coating being operable to provide an elongate bearing surface between the tubular members of said surgical cutting instrument.

2. The instrument according to claim 1, wherein said tin-nickel alloy comprises from about 60 to about 70% tin and from about 40 to 30% nickel.

3. The instrument according to claim 1, wherein said tubular members are made of electropolished stainless steel.

4. The instrument according to claim 3, wherein said coating of tin-nickel alloy is electroplated on the outer surface of the inner tubular member.

5. The instrument according to claim 4, wherein said tin-nickel alloy comprises from about 60 to about 70% tin and from about 40 to 30% nickel.

* * * * *